US00PP14403P39

(12) United States Plant Patent
Pieters

(10) Patent No.: US PP14,403 P3
(45) Date of Patent: Dec. 23, 2003

(54) CHRYSANTHEMUM PLANT NAMED 'GEDI TWO FIG'

(50) Latin Name: *Chrysanthemum morifolium*
Varietal Denomination: Gedi Two Fig

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,793

(22) Filed: May 1, 2002

(65) Prior Publication Data

US 2003/0208813 P1 Nov. 6, 2003

(51) Int. Cl.[7] ..... A01H 5/00
(52) U.S. Cl. ..... Plt./289
(58) Field of Search ..... Plt./289, 287

(56) References Cited

U.S. PATENT DOCUMENTS

PP11,344 P 4/2000 Pieters ..... Plt./290

OTHER PUBLICATIONS

Brummitt, Horticultural Science Chrysanthemum once again, The Garden, 1997, pp. 662–663.*

* cited by examiner

*Primary Examiner*—Bruce R. Campell
*Assistant Examiner*—June Hu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 49 days of short day length, free branching habit, yellow ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Fig.'

BACKGROUND OF THE INVENTION

The new cultivar is a product of hybridization of a female parent Chrysanthemum plant variety 'Sapiro Orange' (undistributed in the United States) and a male parent Chrysanthemum plant variety 'Gedi VL8' (U.S. Plant Pat. No. 11,344). The new cultivar was discovered and selected by the inventor in October 1996.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Fig' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Fig.' These characteristics in combination distinguish 'Gedi Two Fig' as a new and distinct Chrysanthemum cultivar:

1. Decorative-type inflorescence,
2. Consistent flowering response to short days, blooming consistently after 49 days of short day length, 3. Free branching habit,
4. Yellow ray florets,
5. Very uniform round growth habit, and
6. Large quantity of blooms per flowering branch.

Plants of the new cultivar are similar to plants of the female parent variety, 'Sapiro Orange' in most horticultural characteristics, however plants of the new cultivar have a wider diameter inflorescence and ray florets of a different color than plants of the female parent variety. Plants of the new variety also naturally bloom two weeks earlier than plants of the female parent variety.

Plants of the new cultivar are similar to plants of the male parent variety, 'Gedi VL8' in most horticultural characteristics, however plants of the new cultivar have ray florets of a different color and more blooms per flowering branch than plants of the male parent variety. Plants of the new cultivar also naturally bloom two weeks earlier than plants of the male parent variety.

In comparison to the commercially available variety 'Gedi One Nov' (U.S. Plant Pat. No. 13,796), 'Gedi Two Fig' blooms two weeks earlier naturally and has an inflorescence of a single color, fewer ray florets, and has blooms with a smaller diameter.

BRIEF DESCRIPTION OF THE PHOTOGRAPH

The photograph shows a plant of 'Gedi Two Fig' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 84 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Fig'.
Commercial classification: Garden-type Chrysanthemum.
Parentage: Hybridization of a female parent Chrysanthemum plant variety, 'Sapiro Orange' (undistributed in the United States), and a male parent Chrysanthemum plant variety 'Gedi VL8' (U.S. Plant Pat. No. 11,344).

PROPAGATION

Time to rooting: 7 to 14 days at approximately 21° C.
Root description: Fine, fibrous.

PLANT

Growth habit: Mounding herbaceous perennial.
Height: Approximately 18.5 cm.
Spread: Approximately 22.5 cm.
Growth rate: Moderate.
Branching characteristics: Free Branching.
Length of lateral branches: Approximately 19 cm.
Number of leaves per lateral branch: Approximately 41.

FOLIAGE

Leaf:
- *Arrangement.*—Alternate.
- *Average length.*—Approximately 4.5 cm.
- *Average width.*—Approximately 3.9 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137B. Young foliage under side: Near 138A. Mature foliage upper side: Near 137A. Mature foliage under side: Near 138A. Venation upper side: Near 138B. Venation under side: Near 139C.
- *Venation type.*—Palmately net.

Petiole:
- *Average length.*—Approximately 2 cm.
- *Color.*—Near 137A.
- *Diameter.*—Approximately 0.2 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the last two weeks of August.
- *Number of inflorescences per lateral branch.*—Approximately 15.
- *Inflorescence diameter.*—Approximately 3.7 cm.
- *Inflorescence depth.*—Approximately 1.3 cm.
- *Inflorescence longevity on plant.*—Approximately 21 days.
- *Persistence.*—Persistent.

Ray florets:
- *Appearance.*—Matte.
- *Texture.*—Smooth.
- *Average number per flower.*—162.
- *Shape.*—Oblong.
- *Aspect.*—Flat.
- *Margin.*—Entire.
- *Apex.*—Retuse.
- *Length.*—Approximately 1.5 cm.
- *Width.*—Approximately 0.6 cm.
- *Color.*—Upper surface at first opening: Near 13A with near 17A around apex margin. Upper surface at maturity: Near 14A with center one-quarter of ray florets having near 167C around apex margin. Upper surface at fading: Near 13A. Under surface at first opening: Near 17C with near 167B around apex margin. Under surface at maturity. Near 14B with middle one-quarter of ray florets having near 167B around apex margin. Under surface at fading: Near 13C.

Disc florets:
- *Appearance.*—Shiny.
- *Texture.*—Smooth.
- *Average number per flower.*—Approximately 7.
- *Shape.*—Cylindric.
- *Apex.*—Obtuse.
- *Average length.*—Approximately 0.5 cm.
- *Average width.*—Approximately 0.1 cm.
- *Color.*—At first opening: Near 154C. At maturity: Near 15A. At fading. Near 17C.

Peduncle:
- *Length.*—At terminal end (shortest): Approximately 2 cm. At lateral end (longest): Approximately 3.2 cm.
- *Angle to stem.*—Acute.
- *Strength.*—Moderate.
- *Color.*—Near 139C.
- *Habit.*—Upright.
- *Diameter.*—Approximately 0.2 cm.
- *Surface texture.*—Lightly pubescent.

Inflorescence bud:
- *Length.*—Approximately 0.6 cm.
- *Diameter.*—Approximately 0.8 cm.
- *Form.*—Globular.
- *Color.*—Near 14B.

Involucral bracts (phyllaries):
- *Appearance.*—Matte.
- *Texture.*—Lightly pubescent.
- *Number.*—Approximately 43.
- *Shape.*—Oblanceolate.
- *Margin.*—Entire.
- *Apex.*—Acute.
- *Length.*—Approximately 0.5 cm.
- *Width.*—Approximately 0.3 cm.
- *Color.*—Upper side. Near 138A. Under side: Near 138A.

REPRODUCTIVE ORGANS

Ray florets:
- *Number of pistils per flower.*—1.
- *Stigma shape.*—2 Branched.
- *Stigma color.*—Near 7B.
- *Style color.*—Near 154D.
- *Style length.*—Approximately 0.4 cm.
- *Stamens.*—Absent.

Disc florets:

*Number of pistils per flower.*—1.

*Stigma shape.*—Two-branched.

*Stigma color.*—Near 13A.

*Style length.*—Approximately 0.4 cm.

*Style color.*—Near 154D.

*Number of stamens per flower.*—5.

*Anther shape.*—Tubular. Anther color: Near 13A. Pollen color: Dark yellow, Near 13A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Fig' as herein illustrated and described.

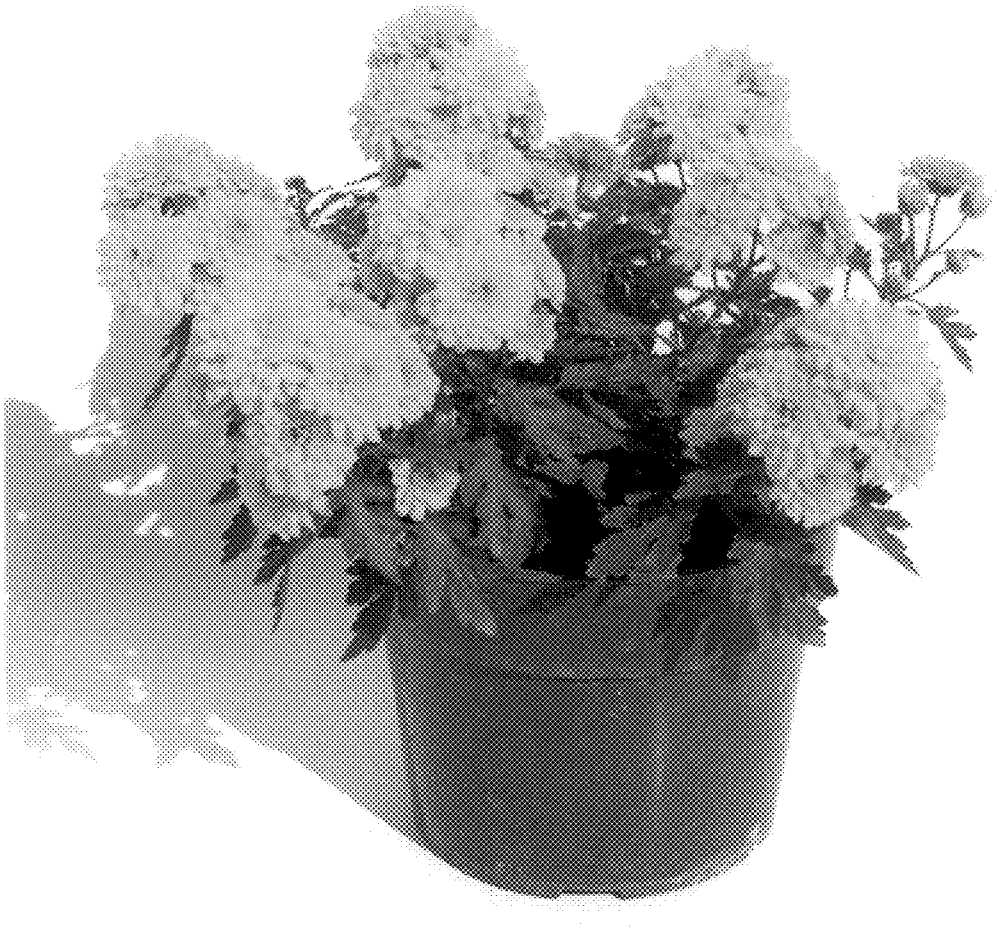

* * * * *